(12) United States Patent
Boulais

(10) Patent No.: US 9,439,557 B2
(45) Date of Patent: Sep. 13, 2016

(54) ARTICULATION JOINT

(75) Inventor: Dennis R. Boulais, Danielson, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1392 days.

(21) Appl. No.: 13/240,884

(22) Filed: Sep. 22, 2011

(65) Prior Publication Data

US 2012/0245418 A1 Sep. 27, 2012

Related U.S. Application Data

(63) Continuation of application No. 11/215,704, filed on Aug. 30, 2005, now Pat. No. 8,052,597.

(51) Int. Cl.
*A61B 1/00* (2006.01)
*A61M 25/00* (2006.01)
*A61B 17/00* (2006.01)
*A61B 1/005* (2006.01)

(52) U.S. Cl.
CPC ........... *A61B 1/0055* (2013.01); *A61B 1/0011* (2013.01); *A61B 1/00103* (2013.01); *Y10T 29/4998* (2015.01)

(58) Field of Classification Search
USPC ........ 600/127–130, 139–152, 104, 106, 107; 604/523–528; 606/1
See application file for complete search history.

(56) References Cited

U.S. PATENT DOCUMENTS

| | | |
|---|---|---|
| 3,470,876 A | 10/1969 | Barchilon |
| 3,572,325 A | 3/1971 | Bazell et al. |
| 3,581,738 A | 6/1971 | Moore |
| 4,108,211 A | 8/1978 | Tanaka |
| 4,286,585 A | 9/1981 | Ogawa |
| 4,294,162 A | 10/1981 | Fowler et al. |
| 4,315,309 A | 2/1982 | Coli |
| 4,351,323 A | 9/1982 | Ouchi et al. |
| 4,425,113 A | 1/1984 | Bilstad |
| 4,432,349 A | 2/1984 | Oshiro |
| 4,471,766 A | 9/1984 | Terayama |
| 4,473,841 A | 9/1984 | Murakoshi et al. |
| 4,488,039 A | 12/1984 | Sato et al. |
| 4,491,865 A | 1/1985 | Danna et al. |
| 4,495,134 A | 1/1985 | Ouchi et al. |
| 4,499,895 A | 2/1985 | Takayama |
| 4,513,235 A | 4/1985 | Acklam et al. |
| 4,515,444 A | 5/1985 | Prescott et al. |
| 4,516,063 A | 5/1985 | Kaye et al. |
| 4,519,391 A | 5/1985 | Murakoshi |
| 4,559,928 A | 12/1985 | Takayama |
| 4,573,450 A | 3/1986 | Arakawa |
| 4,580,210 A | 4/1986 | Nordstrom |

(Continued)

FOREIGN PATENT DOCUMENTS

| | | |
|---|---|---|
| EP | 0 689 851 | 1/1996 |
| EP | 1 300 883 | 4/2003 |

(Continued)

*Primary Examiner* — Ryan Henderson
(74) *Attorney, Agent, or Firm* — Bookoff McAndrews, PLLC

(57) ABSTRACT

In one aspect, the present invention is an articulation joint for use in a low cost medical device such as an endoscope intended for a single use. In one embodiment, the articulation joint comprises a plurality of interconnected segments. In another embodiment, the articulation joint comprises an elongated tubular body. In another aspect, the present invention provides methods of manufacturing an articulation joint for use in a medical device.

20 Claims, 8 Drawing Sheets

(56) References Cited

U.S. PATENT DOCUMENTS

| | | | |
|---|---|---|---|
| 4,586,923 | A | 5/1986 | Gould et al. |
| 4,615,330 | A | 10/1986 | Nagasaki et al. |
| 4,616,630 | A | 10/1986 | Arakawa |
| 4,617,915 | A | 10/1986 | Arakawa |
| 4,621,618 | A | 11/1986 | Omagari et al. |
| 4,625,714 | A | 12/1986 | Toyota |
| 4,631,582 | A | 12/1986 | Nagasaki et al. |
| 4,633,303 | A | 12/1986 | Nagasaki et al. |
| 4,633,304 | A | 12/1986 | Nagasaki |
| 4,643,170 | A | 2/1987 | Miyazaki et al. |
| 4,646,723 | A | 3/1987 | Arakawa |
| 4,649,904 | A | 3/1987 | Krauter et al. |
| 4,651,202 | A | 3/1987 | Arakawa |
| 4,652,093 | A | 3/1987 | Stephen et al. |
| 4,652,916 | A | 3/1987 | Suzaki et al. |
| 4,654,701 | A | 3/1987 | Yabe |
| RE32,421 | E | 5/1987 | Hattori |
| 4,662,725 | A | 5/1987 | Nisioka |
| 4,663,657 | A | 5/1987 | Nagasaki et al. |
| 4,667,655 | A | 5/1987 | Ogiu et al. |
| 4,674,844 | A | 6/1987 | Nishioka et al. |
| 4,686,963 | A | 8/1987 | Cohen et al. |
| 4,697,210 | A | 9/1987 | Toyota et al. |
| 4,700,693 | A | 10/1987 | Lia et al. |
| 4,714,075 | A | 12/1987 | Krauter et al. |
| 4,716,457 | A | 12/1987 | Matsuo |
| 4,719,508 | A | 1/1988 | Sasaki et al. |
| 4,727,417 | A | 2/1988 | Kanno et al. |
| 4,727,418 | A | 2/1988 | Kato et al. |
| 4,745,470 | A | 5/1988 | Yabe et al. |
| 4,745,471 | A | 5/1988 | Takamura et al. |
| 4,746,974 | A | 5/1988 | Matsuo |
| 4,748,970 | A | 6/1988 | Nakajima |
| 4,755,029 | A | 7/1988 | Okabe |
| 4,762,119 | A | 8/1988 | Allred et al. |
| 4,765,312 | A | 8/1988 | Sasa et al. |
| 4,766,489 | A | 8/1988 | Kato |
| 4,787,369 | A | 11/1988 | Allred et al. |
| 4,790,294 | A | 12/1988 | Allred et al. |
| 4,794,913 | A | 1/1989 | Shimonaka et al. |
| 4,796,607 | A | 1/1989 | Allred et al. |
| 4,800,869 | A | 1/1989 | Nakajima |
| 4,805,596 | A | 2/1989 | Hatori |
| 4,806,011 | A | 2/1989 | Bettinger |
| 4,819,065 | A | 4/1989 | Eino |
| 4,819,077 | A | 4/1989 | Kikuchi et al. |
| 4,821,116 | A | 4/1989 | Nagasaki et al. |
| 4,824,225 | A | 4/1989 | Nishioka |
| 4,831,437 | A | 5/1989 | Nishioka et al. |
| 4,836,187 | A | 6/1989 | Iwakoshi et al. |
| 4,844,052 | A | 7/1989 | Iwakoshi et al. |
| 4,845,553 | A | 7/1989 | Konomura et al. |
| 4,845,555 | A | 7/1989 | Yabe et al. |
| 4,847,694 | A | 7/1989 | Nishihara |
| 4,853,772 | A | 8/1989 | Kikuchi |
| 4,860,731 | A | 8/1989 | Matsuura |
| 4,867,546 | A | 9/1989 | Nishioka et al. |
| 4,868,647 | A | 9/1989 | Uehara et al. |
| 4,869,237 | A | 9/1989 | Eino et al. |
| 4,873,965 | A | 10/1989 | Danieli |
| 4,875,468 | A | 10/1989 | Krauter et al. |
| 4,877,314 | A | 10/1989 | Kanamori |
| 4,882,623 | A | 11/1989 | Uchikubo |
| 4,884,134 | A | 11/1989 | Tsuji et al. |
| 4,885,634 | A | 12/1989 | Yabe |
| 4,890,159 | A | 12/1989 | Ogiu |
| 4,894,715 | A | 1/1990 | Uchikubo et al. |
| 4,895,431 | A | 1/1990 | Tsujiuchi et al. |
| 4,899,731 | A | 2/1990 | Takayama et al. |
| 4,899,732 | A | 2/1990 | Cohen |
| 4,899,787 | A | 2/1990 | Ouchi et al. |
| 4,905,666 | A | 3/1990 | Fukuda |
| 4,918,521 | A | 4/1990 | Yabe et al. |
| 4,919,112 | A | 4/1990 | Siegmund |
| 4,919,114 | A | 4/1990 | Miyazaki |
| 4,920,980 | A | 5/1990 | Jackowski |
| 4,928,172 | A | 5/1990 | Uehara et al. |
| 4,931,867 | A | 6/1990 | Kikuchi |
| 4,941,454 | A | 7/1990 | Wood et al. |
| 4,941,456 | A | 7/1990 | Wood et al. |
| 4,951,134 | A | 8/1990 | Nakasima et al. |
| 4,951,135 | A | 8/1990 | Sasagawa et al. |
| 4,952,040 | A | 8/1990 | Igarashi |
| 4,960,127 | A | 10/1990 | Noce et al. |
| 4,961,110 | A | 10/1990 | Nakamura |
| 4,967,269 | A | 10/1990 | Sasagawa et al. |
| 4,971,034 | A | 11/1990 | Doi et al. |
| 4,973,311 | A | 11/1990 | Iwakoshi et al. |
| 4,979,497 | A | 12/1990 | Matsuura et al. |
| 4,982,725 | A | 1/1991 | Hibino et al. |
| 4,984,878 | A | 1/1991 | Miyano |
| 4,986,642 | A | 1/1991 | Yokota et al. |
| 4,987,884 | A | 1/1991 | Nishioka et al. |
| 4,989,075 | A | 1/1991 | Ito |
| 4,989,581 | A | 2/1991 | Tamburrino et al. |
| 4,996,974 | A | 3/1991 | Ciarlei |
| 4,996,975 | A | 3/1991 | Nakamura |
| 5,001,556 | A | 3/1991 | Nakamura et al. |
| 5,005,558 | A | 4/1991 | Aomori |
| 5,005,957 | A | 4/1991 | Kanamori et al. |
| 5,007,408 | A | 4/1991 | Ieoka |
| 5,018,509 | A | 5/1991 | Suzuki et al. |
| 5,022,382 | A | 6/1991 | Ohshoki et al. |
| 5,029,016 | A | 7/1991 | Hiyama et al. |
| 5,034,888 | A | 7/1991 | Uehara et al. |
| 5,040,069 | A | 8/1991 | Matsumoto et al. |
| RE33,689 | E | 9/1991 | Nishioka et al. |
| 5,045,935 | A | 9/1991 | Kikuchi |
| 5,049,989 | A | 9/1991 | Tsuji |
| 5,050,584 | A | 9/1991 | Matsuura |
| 5,050,974 | A | 9/1991 | Takasugi et al. |
| 5,056,503 | A | 10/1991 | Nagasaki |
| 5,061,994 | A | 10/1991 | Takahashi |
| 5,068,719 | A | 11/1991 | Tsuji |
| 5,081,524 | A | 1/1992 | Tsuruoka et al. |
| 5,087,989 | A | 2/1992 | Igarashi |
| 5,110,645 | A | 5/1992 | Matsumoto et al. |
| 5,111,281 | A | 5/1992 | Sekiguchi |
| 5,111,306 | A | 5/1992 | Kanno et al. |
| 5,111,804 | A | 5/1992 | Funakoshi |
| 5,113,254 | A | 5/1992 | Kanno et al. |
| 5,119,238 | A | 6/1992 | Igarashi |
| 5,131,393 | A | 7/1992 | Ishiguro et al. |
| 5,137,013 | A | 8/1992 | Chiba et al. |
| 5,140,265 | A | 8/1992 | Sakiyama et al. |
| 5,159,446 | A | 10/1992 | Hibino et al. |
| 5,170,775 | A | 12/1992 | Tagami |
| 5,172,225 | A | 12/1992 | Takahashi et al. |
| 5,174,293 | A | 12/1992 | Hagiwara |
| 5,176,629 | A | 1/1993 | Kullas et al. |
| 5,178,129 | A * | 1/1993 | Chikama et al. ............ 600/142 |
| 5,179,935 | A | 1/1993 | Miyagi |
| 5,191,878 | A | 3/1993 | Iida et al. |
| 5,198,931 | A | 3/1993 | Igarashi |
| 5,201,908 | A | 4/1993 | Jones |
| 5,208,702 | A | 5/1993 | Shiraiwa |
| 5,209,220 | A | 5/1993 | Hiyama et al. |
| 5,225,958 | A | 7/1993 | Nakamura |
| 5,228,356 | A | 7/1993 | Chuang |
| 5,243,416 | A | 9/1993 | Nakazawa |
| 5,243,967 | A | 9/1993 | Hibino |
| 5,257,628 | A | 11/1993 | Ishiguro et al. |
| 5,271,381 | A | 12/1993 | Ailinger et al. |
| RE34,504 | E | 1/1994 | Uehara et al. |
| 5,291,010 | A | 3/1994 | Tsuji |
| 5,299,559 | A | 4/1994 | Bruce et al. |
| 5,311,858 | A | 5/1994 | Adair |
| 5,325,845 | A | 7/1994 | Adair et al. |
| 5,331,551 | A | 7/1994 | Tsuruoka et al. |
| 5,342,299 | A | 8/1994 | Snoke et al. |
| 5,347,989 | A | 9/1994 | Monroe et al. |
| 5,374,953 | A | 12/1994 | Sasaki et al. |
| 5,379,757 | A | 1/1995 | Hiyama et al. |
| 5,381,782 | A | 1/1995 | DeLaRama et al. |

(56) References Cited

U.S. PATENT DOCUMENTS

| | | |
|---|---|---|
| 5,390,662 A | 2/1995 | Okada |
| 5,400,769 A | 3/1995 | Tanii et al. |
| 5,402,768 A | 4/1995 | Adair |
| 5,402,769 A | 4/1995 | Tsuji |
| 5,409,485 A | 4/1995 | Suda |
| 5,412,478 A | 5/1995 | Ishihara et al. |
| 5,418,649 A | 5/1995 | Igarashi |
| 5,420,644 A | 5/1995 | Watanabe |
| 5,431,645 A | 7/1995 | Smith et al. |
| 5,434,615 A | 7/1995 | Matsumoto |
| 5,436,640 A | 7/1995 | Reeves |
| 5,436,767 A | 7/1995 | Suzuki et al. |
| 5,440,341 A | 8/1995 | Suzuki et al. |
| 5,464,007 A | 11/1995 | Krauter et al. |
| 5,469,840 A | 11/1995 | Tanii et al. |
| 5,473,235 A | 12/1995 | Lance et al. |
| 5,482,029 A | 1/1996 | Sekiguchi et al. |
| 5,484,407 A | 1/1996 | Osypka |
| 5,485,316 A | 1/1996 | Mori et al. |
| 5,496,260 A | 3/1996 | Krauter et al. |
| 5,515,449 A | 5/1996 | Tsuruoka et al. |
| 5,518,501 A | 5/1996 | Oneda et al. |
| 3,266,059 A | 8/1996 | Stelle |
| 5,543,831 A | 8/1996 | Tsuji et al. |
| 5,569,158 A | 10/1996 | Suzuki et al. |
| 5,569,159 A | 10/1996 | Anderson et al. |
| 5,586,262 A | 12/1996 | Komatsu et al. |
| 5,589,854 A | 12/1996 | Tsai |
| 5,591,202 A | 1/1997 | Slater et al. |
| 5,608,451 A | 3/1997 | Konno et al. |
| 5,619,380 A | 4/1997 | Ogasawara et al. |
| 5,622,528 A | 4/1997 | Hamano et al. |
| 5,631,695 A | 5/1997 | Nakamura et al. |
| 5,633,203 A | 5/1997 | Adair |
| 5,643,203 A | 7/1997 | Beiser et al. |
| 5,645,075 A | 7/1997 | Palmer et al. |
| 5,647,840 A | 7/1997 | D'Amelio et al. |
| 5,658,238 A | 8/1997 | Suzuki et al. |
| 5,667,477 A | 9/1997 | Segawa |
| 5,674,182 A | 10/1997 | Suzuki et al. |
| 5,674,197 A | 10/1997 | van Muiden et al. |
| 5,685,823 A | 11/1997 | Ito et al. |
| 5,685,825 A | 11/1997 | Takase et al. |
| 5,691,853 A | 11/1997 | Miyano |
| 5,695,450 A | 12/1997 | Yabe et al. |
| 5,698,866 A | 12/1997 | Doiron et al. |
| 5,702,349 A | 12/1997 | Morizumi |
| 5,703,724 A | 12/1997 | Miyano |
| 5,704,371 A | 1/1998 | Shepard |
| 5,704,896 A | 1/1998 | Fukunishi et al. |
| 5,708,482 A | 1/1998 | Takahashi et al. |
| 5,721,566 A | 2/1998 | Rosenberg et al. |
| 5,724,068 A | 3/1998 | Sanchez et al. |
| 5,728,045 A | 3/1998 | Komi |
| 5,739,811 A | 4/1998 | Rosenberg et al. |
| 5,740,801 A | 4/1998 | Branson |
| 5,746,696 A | 5/1998 | Kondo |
| 5,749,828 A * | 5/1998 | Solomon ............. A61B 1/0055 600/139 |
| 5,764,809 A | 6/1998 | Nomami et al. |
| 5,767,839 A | 6/1998 | Rosenberg |
| 5,781,172 A | 7/1998 | Engel et al. |
| 5,788,714 A | 8/1998 | Ouchi |
| 5,789,047 A | 8/1998 | Sasaki et al. |
| 5,793,539 A | 8/1998 | Konno et al. |
| 5,805,140 A | 9/1998 | Rosenberg et al. |
| 5,810,715 A | 9/1998 | Moriyama |
| 5,812,983 A | 9/1998 | Kumagai |
| 5,819,736 A | 10/1998 | Avny et al. |
| 5,820,591 A | 10/1998 | Thompson et al. |
| 5,821,466 A | 10/1998 | Clark et al. |
| 5,821,920 A | 10/1998 | Rosenberg et al. |
| 5,823,948 A | 10/1998 | Ross, Jr. et al. |
| 5,827,186 A | 10/1998 | Chen et al. |
| 5,827,190 A | 10/1998 | Palcic et al. |
| 5,828,197 A | 10/1998 | Martin et al. |
| 5,828,363 A | 10/1998 | Yaniger et al. |
| 5,830,124 A | 11/1998 | Suzuki et al. |
| 5,830,128 A | 11/1998 | Tanaka |
| 5,836,869 A | 11/1998 | Kudo et al. |
| 5,837,023 A | 11/1998 | Koike et al. |
| 5,840,014 A | 11/1998 | Miyano et al. |
| 5,841,126 A | 11/1998 | Fossum et al. |
| 5,843,000 A | 12/1998 | Nishioka et al. |
| 5,846,183 A | 12/1998 | Chilcoat |
| 5,855,560 A | 1/1999 | Idaomi et al. |
| 5,857,963 A | 1/1999 | Pelchy et al. |
| 5,865,724 A | 2/1999 | Palmer et al. |
| 5,868,664 A | 2/1999 | Speier et al. |
| 5,868,666 A | 2/1999 | Okada et al. |
| 5,873,816 A | 2/1999 | Kagawa et al. |
| 5,873,866 A | 2/1999 | Kondo et al. |
| 5,876,326 A | 3/1999 | Takamura et al. |
| 5,876,331 A | 3/1999 | Wu et al. |
| 5,876,373 A | 3/1999 | Giba et al. |
| 5,876,427 A | 3/1999 | Chen et al. |
| 5,877,819 A | 3/1999 | Branson |
| 5,879,284 A | 3/1999 | Tsujita |
| 5,880,714 A | 3/1999 | Rosenberg et al. |
| 5,882,293 A | 3/1999 | Ouchi |
| 5,882,339 A | 3/1999 | Beiser et al. |
| 5,889,670 A | 3/1999 | Schuler et al. |
| 5,889,672 A | 3/1999 | Schuler et al. |
| 5,892,630 A | 4/1999 | Broome |
| 5,895,350 A | 4/1999 | Hori |
| 5,897,507 A | 4/1999 | Kortenbach et al. |
| 5,897,525 A | 4/1999 | Dey et al. |
| 5,907,487 A | 5/1999 | Rosenberg et al. |
| 5,923,018 A | 7/1999 | Kameda et al. |
| 5,928,136 A | 7/1999 | Barry |
| 5,929,607 A | 7/1999 | Rosenberg et al. |
| 5,929,846 A | 7/1999 | Rosenberg et al. |
| 5,929,900 A | 7/1999 | Yamanaka et al. |
| 5,929,901 A | 7/1999 | Adair et al. |
| 5,931,833 A | 8/1999 | Silverstein |
| 5,933,809 A | 8/1999 | Hunt et al. |
| 5,935,085 A | 8/1999 | Welsh et al. |
| 5,936,778 A | 8/1999 | Miyano et al. |
| 5,941,817 A | 8/1999 | Crawford |
| 5,950,168 A | 9/1999 | Simborg et al. |
| 5,951,462 A | 9/1999 | Yamanaka |
| 5,956,416 A | 9/1999 | Tsuruoka et al. |
| 5,956,689 A | 9/1999 | Everhart |
| 5,956,690 A | 9/1999 | Haggerson et al. |
| 5,959,613 A | 9/1999 | Rosenberg et al. |
| 5,976,070 A | 11/1999 | Ono et al. |
| 5,976,074 A | 11/1999 | Moriyama |
| 5,980,454 A | 11/1999 | Broome |
| 5,980,468 A | 11/1999 | Zimmon |
| 5,986,693 A | 11/1999 | Adair et al. |
| 5,991,729 A | 11/1999 | Barry et al. |
| 5,991,730 A | 11/1999 | Lubin et al. |
| 5,999,168 A | 12/1999 | Rosenberg et al. |
| 6,002,425 A | 12/1999 | Yamanaka et al. |
| 6,007,531 A | 12/1999 | Snoke et al. |
| 6,014,630 A | 1/2000 | Jeacock et al. |
| 6,015,088 A | 1/2000 | Parker et al. |
| 6,017,322 A | 1/2000 | Snoke et al. |
| 6,020,875 A | 2/2000 | Moore et al. |
| 6,020,876 A | 2/2000 | Rosenberg et al. |
| 6,026,363 A | 2/2000 | Shepard |
| 6,030,360 A | 2/2000 | Biggs |
| 6,032,120 A | 2/2000 | Rock et al. |
| 6,039,728 A | 3/2000 | Berlien et al. |
| 6,043,839 A | 3/2000 | Adair et al. |
| 6,050,718 A | 4/2000 | Schena et al. |
| 6,057,828 A | 5/2000 | Rosenberg et al. |
| 6,059,719 A | 5/2000 | Yamamoto et al. |
| 6,061,004 A | 5/2000 | Rosenberg |
| 6,067,077 A | 5/2000 | Martin et al. |
| 6,071,248 A | 6/2000 | Zimmon |
| 6,075,555 A | 6/2000 | Street |
| 6,078,308 A | 6/2000 | Rosenberg et al. |
| 6,078,353 A | 6/2000 | Yamanaka et al. |

(56) References Cited

U.S. PATENT DOCUMENTS

| | | | |
|---|---|---|---|
| 6,078,876 A | 6/2000 | Rosenberg et al. |
| 6,080,104 A | 6/2000 | Ozawa et al. |
| 6,081,809 A | 6/2000 | Kumagai |
| 6,083,152 A | 7/2000 | Strong |
| 6,083,170 A | 7/2000 | Ben-Haim |
| 6,095,971 A | 8/2000 | Takahashi |
| 6,099,465 A | 8/2000 | Inoue |
| 6,100,874 A | 8/2000 | Schena et al. |
| 6,104,382 A | 8/2000 | Martin et al. |
| 6,120,435 A | 9/2000 | Eino |
| 6,125,337 A | 9/2000 | Rosenberg et al. |
| 6,128,006 A | 10/2000 | Rosenberg et al. |
| 6,132,369 A | 10/2000 | Takahashi |
| 6,134,056 A | 10/2000 | Nakamuka |
| 6,134,506 A | 10/2000 | Rosenberg et al. |
| 6,135,946 A | 10/2000 | Konen et al. |
| 6,139,508 A | 10/2000 | Simpson et al. |
| 6,141,037 A | 10/2000 | Upton et al. |
| 6,142,956 A | 11/2000 | Kortenbach et al. |
| 6,146,355 A | 11/2000 | Biggs |
| 6,149,607 A | 11/2000 | Simpson et al. |
| 6,152,877 A | 11/2000 | Masters |
| 6,154,198 A | 11/2000 | Rosenberg |
| 6,154,248 A | 11/2000 | Ozawa et al. |
| 6,155,988 A | 12/2000 | Peters |
| 6,181,481 B1 | 1/2001 | Yamamoto et al. |
| 6,184,922 B1 | 2/2001 | Saito et al. |
| 6,193,714 B1 | 2/2001 | McGaffigan et al. |
| 6,195,592 B1 | 2/2001 | Schuler et al. |
| 6,203,493 B1 | 3/2001 | Ben-Haim |
| 6,206,824 B1 | 3/2001 | Ohara et al. |
| 6,211,904 B1 | 4/2001 | Adair |
| 6,216,104 B1 | 4/2001 | Moshfeghi et al. |
| 6,219,091 B1 | 4/2001 | Yamanaka et al. |
| 6,221,070 B1 | 4/2001 | Tu et al. |
| 6,241,668 B1 | 6/2001 | Herzog |
| 6,260,994 B1 | 7/2001 | Matsumoto et al. |
| 6,270,453 B1 | 8/2001 | Sakai |
| 6,272,470 B1 | 8/2001 | Teshima |
| 6,275,255 B1 | 8/2001 | Adair et al. |
| 6,283,960 B1 | 9/2001 | Ashley |
| 6,295,082 B1 | 9/2001 | Dowdy et al. |
| 6,299,625 B1 | 10/2001 | Bacher |
| 6,309,347 B1 | 10/2001 | Takahashi et al. |
| 6,310,642 B1 | 10/2001 | Adair et al. |
| 6,319,196 B1 | 11/2001 | Minami |
| 6,319,197 B1 | 11/2001 | Tsuji et al. |
| 6,334,844 B1 | 1/2002 | Akiba |
| 6,346,075 B1 | 2/2002 | Arai et al. |
| 6,366,799 B1 | 4/2002 | Acker et al. |
| 6,381,029 B1 | 4/2002 | Tipirneni |
| 6,398,724 B1 | 6/2002 | May et al. |
| 6,413,207 B1 | 7/2002 | Minami |
| 6,421,078 B1 | 7/2002 | Akai et al. |
| 6,425,535 B1 | 7/2002 | Akiba |
| 6,425,858 B1 | 7/2002 | Minami |
| 6,436,032 B1 | 8/2002 | Eto et al. |
| 6,441,845 B1 | 8/2002 | Matsumoto |
| 6,447,444 B1 | 9/2002 | Avni et al. |
| 6,449,006 B1 | 9/2002 | Shipp |
| 6,453,190 B1 | 9/2002 | Acker et al. |
| 6,454,162 B1 | 9/2002 | Teller |
| 6,459,447 B1 | 10/2002 | Okada et al. |
| 6,468,204 B2 | 10/2002 | Sendai et al. |
| 6,475,141 B2 | 11/2002 | Abe |
| 6,478,730 B1 | 11/2002 | Bala et al. |
| 6,482,149 B1 | 11/2002 | Torii |
| 6,489,987 B1 | 12/2002 | Higuchi et al. |
| 6,496,827 B2 | 12/2002 | Kozam et al. |
| 6,498,948 B1 | 12/2002 | Ozawa et al. |
| 6,503,193 B1 | 1/2003 | Iwasaki et al. |
| 6,506,196 B1 | 1/2003 | Laufer |
| 6,520,908 B1 | 2/2003 | Ikeda et al. |
| 6,524,234 B2 | 2/2003 | Ouchi |
| 6,530,882 B1 | 3/2003 | Farkas et al. |
| 6,533,722 B2 | 3/2003 | Nakashima |
| 6,540,669 B2 | 4/2003 | Abe et al. |
| 6,544,194 B1 | 4/2003 | Kortenbach et al. |
| 6,545,703 B1 | 4/2003 | Takahashi et al. |
| 6,551,239 B2 | 4/2003 | Renner et al. |
| 6,558,317 B2 | 5/2003 | Takahashi et al. |
| 6,561,971 B1 | 5/2003 | Akiba |
| 6,565,507 B2 | 5/2003 | Kamata et al. |
| 6,574,629 B1 | 6/2003 | Cooke, Jr. et al. |
| 6,589,162 B2 | 7/2003 | Nakashima et al. |
| 6,595,913 B2 | 7/2003 | Takahashi |
| 6,597,390 B1 | 7/2003 | Higuchi |
| 6,599,239 B2 | 7/2003 | Hayakawa et al. |
| 6,602,186 B1 | 8/2003 | Sugimoto et al. |
| 6,605,035 B2 | 8/2003 | Ando et al. |
| 6,609,135 B1 | 8/2003 | Omori et al. |
| 6,611,846 B1 | 8/2003 | Stoodley |
| 6,614,969 B2 | 9/2003 | Eichelberger et al. |
| 6,616,601 B2 | 9/2003 | Hayakawa |
| 6,623,424 B2 | 9/2003 | Hayakawa et al. |
| 6,638,214 B2 | 10/2003 | Akiba |
| 6,638,215 B2 | 10/2003 | Kobayashi |
| 6,641,528 B2 | 11/2003 | Torii |
| 6,651,669 B1 | 11/2003 | Burnside |
| 6,656,110 B1 | 12/2003 | Irion et al. |
| 6,656,112 B2 | 12/2003 | Miyanaga |
| 6,659,940 B2 | 12/2003 | Adler |
| 6,663,561 B2 | 12/2003 | Sugimoto et al. |
| 6,669,629 B2 | 12/2003 | Matsui |
| 6,673,012 B2 | 1/2004 | Fujii et al. |
| 6,677,984 B2 | 1/2004 | Kobayashi et al. |
| 6,678,397 B1 | 1/2004 | Ohmori et al. |
| 6,682,479 B1 | 1/2004 | Takahashi et al. |
| 6,685,631 B2 | 2/2004 | Minami |
| 6,686,949 B2 | 2/2004 | Kobayashi et al. |
| 6,690,409 B1 | 2/2004 | Takahashi |
| 6,690,963 B2 | 2/2004 | Ben-Haim et al. |
| 6,692,431 B2 | 2/2004 | Kazakevich |
| 6,697,101 B1 | 2/2004 | Takahashi et al. |
| 6,699,181 B2 | 3/2004 | Wako |
| 6,702,737 B2 | 3/2004 | Hinto et al. |
| 6,711,426 B2 | 3/2004 | Benaron et al. |
| 6,715,068 B1 | 3/2004 | Abe |
| 6,716,162 B2 | 4/2004 | Hakamata |
| 6,728,599 B2 | 4/2004 | Wang et al. |
| 6,730,018 B2 | 5/2004 | Takase |
| 6,736,773 B2 | 5/2004 | Wendlandt et al. |
| 6,743,240 B2 | 6/2004 | Smith et al. |
| 6,749,559 B1 | 6/2004 | Kraas et al. |
| 6,749,560 B1 | 6/2004 | Konstoram et al. |
| 6,749,561 B2 | 6/2004 | Kazakevich |
| 6,753,905 B1 | 6/2004 | Okada et al. |
| 6,758,806 B2 | 7/2004 | Kamrava et al. |
| 6,758,807 B2 | 7/2004 | Minami |
| 6,758,842 B2 | 7/2004 | Irion et al. |
| 6,778,208 B2 | 8/2004 | Takeshige et al. |
| 6,780,151 B2 | 8/2004 | Grabover et al. |
| 6,785,410 B2 | 8/2004 | Vining et al. |
| 6,785,593 B2 | 8/2004 | Wang et al. |
| 6,796,938 B2 | 9/2004 | Sendai |
| 6,796,939 B1 | 9/2004 | Hirata et al. |
| 6,798,533 B2 | 9/2004 | Tipimeni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang et al. |
| 6,842,196 B1 | 1/2005 | Swift et al. |
| 6,846,286 B2 | 1/2005 | Suzuki et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,858,004 B1 | 2/2005 | Ozawa et al. |
| 6,858,014 B2 | 2/2005 | Damarati |

(56) References Cited

U.S. PATENT DOCUMENTS

| | | |
|---|---|---|
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayashi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami |
| 6,949,068 B2 | 9/2005 | Taniguchi et al. |
| 6,950,691 B2 | 9/2005 | Uchikubo |
| 6,955,671 B2 | 10/2005 | Uchikubo |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0193664 A1 | 12/2002 | Ross et al. |
| 2003/0032863 A1 | 2/2003 | Kazakevich |
| 2003/0036748 A1 | 2/2003 | Cooper |
| 2003/0069897 A1 | 4/2003 | Roy et al. |
| 2003/0149338 A1 | 8/2003 | Francois et al. |
| 2003/0181905 A1 | 9/2003 | Long |
| 2004/0044350 A1* | 3/2004 | Martin et al. ............ 606/139 |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0075538 A1 | 4/2005 | Banik |
| 2005/0197861 A1 | 9/2005 | Omori et al. |
| 2005/0203341 A1 | 9/2005 | Welker et al. |
| 2005/0228697 A1 | 10/2005 | Funahashi |
| 2005/0272978 A1 | 12/2005 | Brunnen et al. |
| 2005/0273085 A1 | 12/2005 | Hinman et al. |
| 2006/0111615 A1 | 5/2006 | Danitz et al. |

FOREIGN PATENT DOCUMENTS

| | | |
|---|---|---|
| JP | 58-78635 | 5/1983 |
| JP | 05-31071 | 2/1993 |
| JP | 05-091972 | 4/1993 |
| JP | 06-105800 | 4/1994 |
| JP | 06-254048 | 9/1994 |
| JP | 07-8441 | 1/1995 |
| JP | 10-113330 | 5/1998 |
| JP | 10-286221 | 10/1998 |
| JP | 11-216113 | 8/1999 |
| JP | 3219521 | 8/2001 |
| JP | 2002 102152 | 4/2002 |
| JP | 2002-177197 | 6/2002 |
| JP | 2002-185873 | 6/2002 |
| JP | 2002-253481 | 9/2002 |
| JP | 3372273 | 11/2002 |
| JP | 2003-75113 | 3/2003 |
| JP | 3482238 | 10/2003 |
| WO | WO 93/13704 | 7/1993 |
| WO | WO 2004/016310 | 2/2004 |
| WO | WO 2005/023082 | 3/2005 |

* cited by examiner

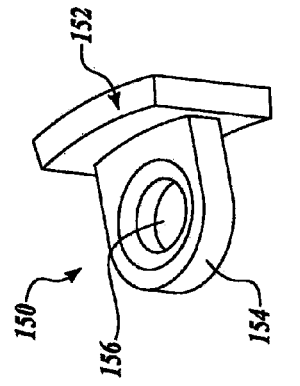
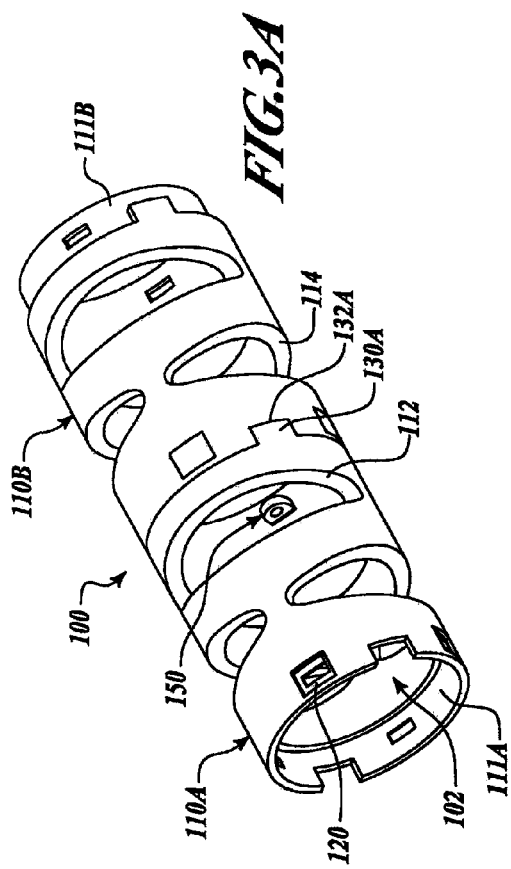
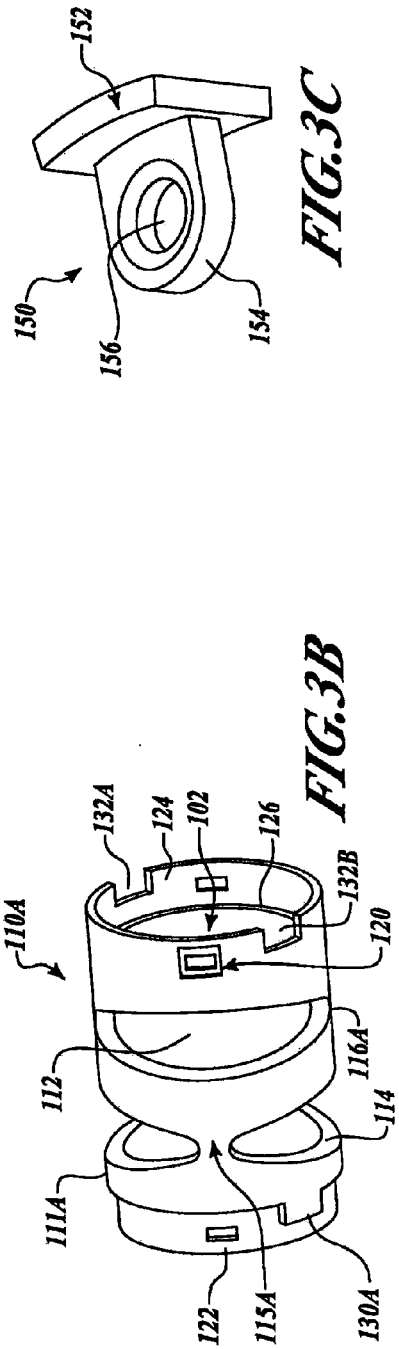

ARTICULATION JOINT

CROSS-REFERENCE TO RELATED APPLICATIONS

This is a Continuation Application of U.S. patent application Ser. No. 11/215,704, filed Aug. 30, 2005 now U.S. Pat. No. 8,052,597, currently pending, which is incorporated herein by reference in its entirety.

FIELD OF THE INVENTION

The present invention relates to medical devices in general and to articulation joints for use in medical devices in particular.

BACKGROUND OF THE INVENTION

It has become well established that there are major health benefits from regular endoscopic examinations of a patient's internal structures such as the alimentary canals and airways, e.g., the esophagus, stomach, lungs, colon, uterus, urethra, kidney, and other organ systems. Endoscopes are also commonly used to perform surgical, therapeutic, diagnostic, or other medical procedures under direct visualization. A conventional imaging endoscope used for such procedures includes an illuminating mechanism such as a fiber optic light guide connected to a proximal source of light, and an imaging means such as an imaging light guide to carry an image to a remote camera, or eye piece, or a miniature video camera within the endoscope itself. In addition, most endoscopes include one or more working channels through which medical devices such as biopsy forceps, snares, fulguration probes and other tools may be passed in order to perform a procedure at a desired location in the patient's body.

Navigation of the endoscope through complex and tortuous paths is critical to the success of the examination with minimum pain, side effects, risk or sedation to the patient. To this end, modern endoscopes include means for deflecting the distal tip of the scope to follow the pathway of the structure under examination, with minimum deflection or friction force upon the surrounding tissue. Control cables similar to bicycle brake cables are carried within the endoscope body in order to connect an articulation joint adjacent to the distal end to a set of control knobs at the proximal endoscope handle. By manipulating the control knobs, the operator is usually able to steer the endoscope during insertion and direct it to a region of interest. Common operator complaints about traditional endoscopes include their limited flexibility, limited column strength, and limited operator control of stiffness along the endoscope length.

Conventional endoscopes are expensive, hand assembled medical devices costing in the range of $25,000 for an endoscope, and much more for the associated operator console. Because of this expense, these conventional endoscopes are built to withstand repeated disinfections and use upon many patients. Conventional endoscopes are generally built of sturdy materials, which decreases the flexibility of the scope and thus can decrease patient comfort. Furthermore, conventional endoscopes are complex and fragile instruments that frequently need expensive repair as a result of damage during use or during a disinfection procedure.

Low cost, disposable medical devices designated for a single use have become popular for instruments that are difficult to clean properly. Single-use, disposable devices are packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. One medical device that has not previously been inexpensive enough to be considered truly disposable is the endoscope, such as a colonoscope, bronchoscope, gastroscope, duodenoscope, etc. Such a single-use or disposable endoscope is described in U.S. patent application Ser. No. 10/811,781, filed Mar. 29, 2004, and in a U.S. Continuation-in-Part patent application Ser. No. 10/956,007, filed Sep. 30, 2004, that are assigned to Scimed Life Systems, Inc., now Boston Scientific Scimed, Inc., and are hereby incorporated by reference.

The articulation joint adjacent to the distal tip of a conventional endoscope is typically made from complicated stamped and formed parts that are brazed together. The brazing operation is expensive and the metal articulation joint segments require special tooling to produce. In addition, adhesives are often used to assemble the articulation joint segments to each other. Therefore, a need exists for a method of producing articulation joints from low cost materials that are easily assembled for use in a low-cost medical device such as a disposable endoscope.

SUMMARY OF THE INVENTION

To address these and other concerns, in one embodiment the present invention is an articulation joint for use in a medical device such as an endoscope. The articulation joint is comprised of a number of low cost, easily mass produced components that allow the distal end of the endoscope to be bent in a desired direction by one or more control cables. In one embodiment, the articulation joint body comprises a plurality of interconnecting segments. Each segment comprises a cylinder with an outer wall and a central lumen. The outer wall includes a number of hinge elements therein and a series of slots therethrough. A plurality of cable guide elements having a passage for control cables are inserted into the slots and two or more cables are threaded through the plurality of cable guide elements and tensioned to form the articulation joint body.

In another embodiment, the articulation joint body is a tubular body comprising a cylinder with an outer wall and a central lumen. The outer wall includes a number of hinge elements therein and a series of slots therethrough. A plurality of annular rings are snap-fitted around the circumference of the tubular body at spaced intervals. Each annular ring has an outer circumference with a first end and a second end and a space therebetween. Also included in each annular ring is at least one pair of inwardly extending cable guide loops adapted to be inserted into the slots in the outer wall of the tubular body. Two or more cables are threaded through the plurality of cable guide loops and tensioned to form the articulation joint body.

In another aspect, the present invention includes a method of manufacturing an articulation joint for use in a medical device. In one embodiment, the method comprises injection molding a plurality of segments having interconnecting structures. Each segment comprises a cylinder with an outer wall and a central lumen. The outer wall includes a number of hinge elements therein and a series of slots therethrough. The method includes injection molding a plurality of cable guide elements that each have a passage element adapted to be inserted through the slots on the outer wall. The method involves interconnecting two or more segments and inserting the cable guide elements into the slots in the outer walls of the segments. One or more cables are then threaded through the guide elements and tensioned to form the articulation joint.

In another embodiment, the method comprises injection molding a tubular body comprising a cylinder with an outer wall and a central lumen. The outer wall includes a number of hinge elements and a series of slots therethrough. A plurality of annular rings are formed, each ring having two or more guide loops sized to be received in the slots in the outer wall. The annular rings are snap-fitted over the tubular body such that the guide loops are fitted through the slots and at least two cables are threaded through the guide loops and tensioned to form the articulation joint.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A illustrates a partial view of an articulation joint body comprising a plurality of interconnected segments in accordance with an embodiment of the present invention;

FIG. 3B is a detailed view of a segment of the articulation joint body shown in FIG. 3A;

FIG. 3C is a perspective view of a cable guide element for use in assembling an articulation joint body comprising a plurality of interconnected segments in accordance with an embodiment of the present invention;

DETAILED DESCRIPTION OF THE PREFERRED EMBODIMENT

Generally described, the present invention provides an articulation joint and a method of making an articulation joint for use in a medical device, such as an endoscope. The present invention provides many advantages over articulation joints used in conventional endoscopy systems. For example, the articulation joints of the present invention are easy to assemble and do not require the use of adhesives or brazing, thereby providing an inexpensive and easily mass-produced joint that allows the distal end of a medical device, such as an endoscope, to be bent in any desired direction by one or more control cables.

The various embodiments of the articulation joint described herein may be used with both conventional reusable endoscopes and low cost, disposable endoscopes, such as those described in U.S. patent application Ser. No. 10/811,781, filed Mar. 29, 2004, and in a U.S. Continuation-in-Part patent application Ser. No. 10/956,007, filed Sep. 30, 2004, that are assigned to Scimed Life Systems, Inc., now Boston Scientific Scimed, Inc., and are hereby incorporated by reference.

Figure 1:
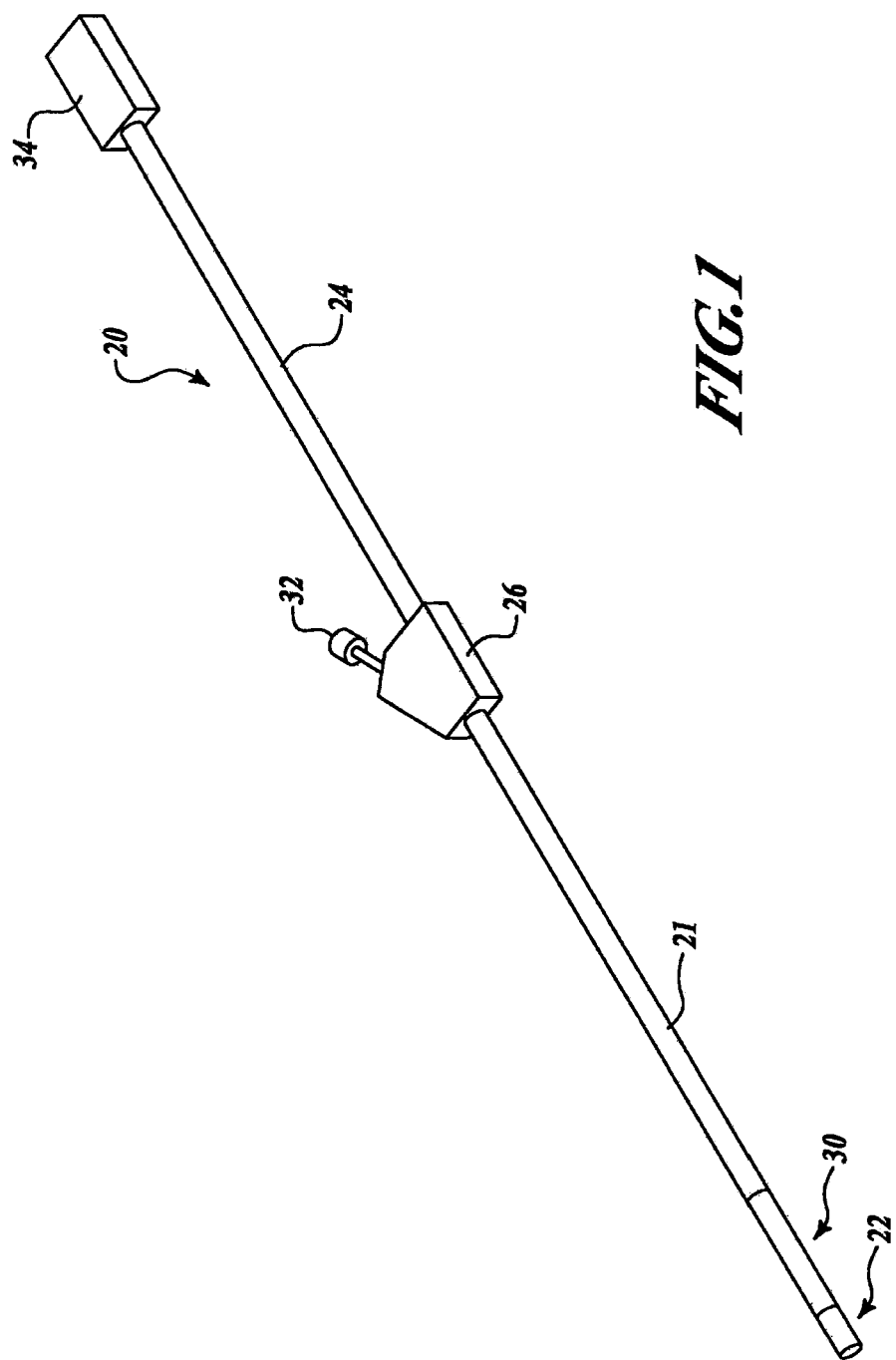
FIG. 1 is a diagram illustrating a representative embodiment of an endoscope having a distal end, a proximal end and an articulation joint adjacent the distal end formed in accordance with an embodiment of the present invention.

FIG. 1 illustrates an exemplary endoscope 20, having an embodiment of an articulation joint 30 formed in accordance with the present invention. The endoscope 20 can be any single-use or reusable, flexible, or partially-flexible elongated probe, such as, for example, a bronchoscope or a colonoscope. In the embodiment shown in FIG. 1, the endoscope 20 includes an elongated shaft 21 with a distal end 22 that is advanced into a patient's body cavity and a proximal end 24 that is removably connected to a control cabinet (not shown) via a connector 34. The endoscope 20 includes the articulation joint 30 proximal to the distal tip 22 to provide sufficient flexibility to the distal section of the shaft 21 such that the distal end 22 can be directed over the required deflection range (180° or more). The endoscope 20 has a set of control cables 40, shown best in FIG. 2, that control the motion of the distal end 22. The distal end of the control cables are attached at or adjacent to the distal end 22 of the shaft, while the proximal ends of the control cables are attached to actuators in a handle (not shown) or in a control unit (not shown).

In the embodiment shown in FIG. 1, the endoscope 20 also includes a breakout box 26 that is positioned approximately midway along the length of the endoscope. The breakout box 26 provides an entrance to a working channel covered by a cap 32. In use, an operator can remove the cap 32 and insert a medical device such as a biopsy forceps, snare, etc., into the working channel of the endoscope to perform a desired procedure within the patient.

Figure 2:
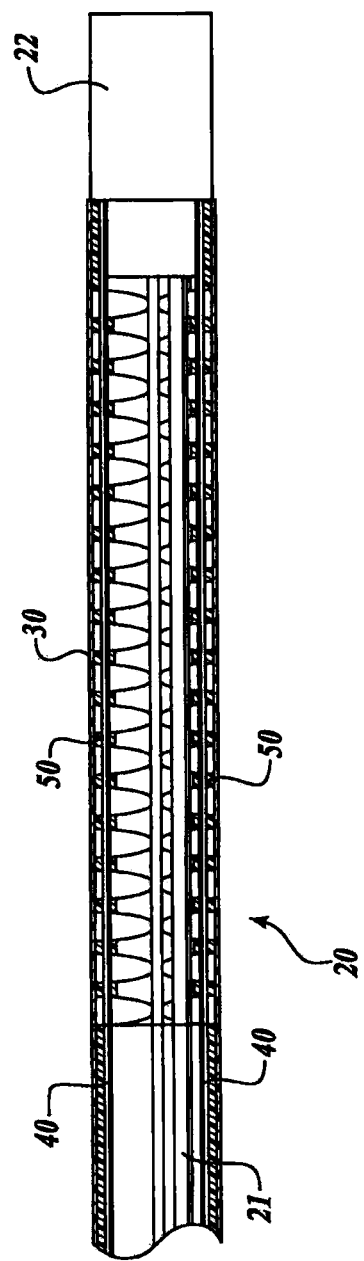
FIG. 2 illustrates an articulation joint positioned adjacent a distal portion of an endoscope shaft in accordance with an embodiment of the present invention.

FIG. 2 is a longitudinal, cross-sectional view of the distal portion of the shaft 21 of the endoscope 20 in accordance with one embodiment of the present invention. The endoscope 20 generally comprises a hollow shaft having one or more lumens formed of plastic materials, such as polyurethane or polyethylene, which terminate at the distal end 22. The shape of the distal end 22 and shaft 21 are usually cylindrical but can be made in other shapes to facilitate passage into a body cavity. The distal end 22 comprises a cap that is secured within a central lumen to the distal end of the articulation joint 30. The distal end of the shaft 21 is secured to the proximal end of the articulation joint 30. In some embodiments, the shaft 21 has a greater torsional stiffness and/or is better able to transmit torque towards the distal end of the endoscope than at the proximal end of the endoscope. The cap at the distal end 22 includes an imaging system with a light illumination port, an image sensor, an opening to a working channel, and a flushing port. Further detail of an exemplary imaging system and its operation can be found in U.S. patent application Ser. Nos. 10/811,781, and 10/956,007, as discussed above.

With continued reference to FIG. 2, a number of control cables 40 extend from the proximal end of the shaft 21 where they connect to actuators in the control cabinet or a manual handle (not shown). The control cables 40 extend through a plurality of cable guide elements 50 positioned along the walls of the articulation joint 30, and terminate either at the distal end of the articulation joint 30 or in the distal end section 22. The proximal portion of the control cables 40 may be routed within the center lumen of the shaft 21, or, as shown in FIG. 2, may be routed through a number of cable guide elements or lumens formed within or along the walls of the shaft 21, as discussed in more detail below.

In accordance with the various aspects of the invention, the articulation joint 30 has a generally cylindrical configuration with a central lumen. In one embodiment, shown in FIG. 3A, an articulation joint body 100 is formed from a plurality of interconnected segments 110A, 110B that are axially aligned and secured to one another to create an articulation joint. FIG. 3B shows further detail of the segment 110A. The articulation joint segment 110 comprises a cylindrical tube having an outer wall 111A and an open central lumen 102. One or more hinges 112, 114 are formed in the outer wall 111A along the longitudinal axes in order to facilitate bending of the assembled articulation joint body 100. In one embodiment, as shown in FIG. 3A, each segment comprises two pairs of hinge elements 112, 114. Each hinge 112, 114 comprises a pair of opposing V-shaped slits in the outer wall 111A that are separated by a pair of opposing flex points 115A, 155B (hidden in FIG. 3B) and 116A, 166B (hidden in FIG. 3B) in the outer wall 111A. Upon tension of the control cables, each hinge allows the segment and/or the assembled tubular body comprising multiple segments to move back and forth in an amount that is determined by the widest part of the V-shaped slits. In the embodiment of the articulation joint body 100 shown in FIG. 3A, the hinges 112 and 114 are circumferentially arranged in an alternating 90 degree pattern to achieve articulation in two planes, although other arrangements would also be known to one of skill in the art. As will be appreciated, the angles of the V-shaped cuts that form the hinges 112 and 114 may be uniform, or may vary along the length of the articulation joint body 100. Similarly, the distance between adjacent hinges 112 and 114 may be uniform or may vary in order to tailor the bending and torque fidelity characteristics of the articulation joint body 100. The segments 110A, 110B, etc., are preferably made from a molded plastic material and include a central lumen 102 through which the control cables 40 and other elements of the endoscope 20 are passed to allow electrical, irrigation and aspiration connections to extend into the distal end 22. Suitable materials for forming the articulation joint segments 110A, 110B include polyurethane, polyethylene, polypropylene or other biocompatible polymers.

The articulation joint body 100 may be formed from any number of interconnecting segments 110A, 110B, etc., in order to provide an articulation joint having any total bend angle required. For example, in one embodiment of the articulation joint body 100, each segment includes the hinge 112 and 114, each having a closing angle of 30 degrees. In accordance with this embodiment, six segments 110A, 110B, 110C, 110D, 110E, and 110F (not shown), having a corresponding total of six hinges 112 and 114 for each axis disposed along the length of the articulation joint are required to provide a 360 degree range of movement.

FIGS. 3A and 3B additionally illustrate a representative set of interconnecting structures capable of interlocking the segments 110A and 110B to form a portion of the articulation joint body 100. As shown in FIG. 3B, the segment 110A comprises an outer wall 111A having a first end 122 and a second end 124. The first end 122 of the segment 110A includes an outwardly extending rim having an outer diameter selected such that the rim is able to be received in a corresponding counter-bored detail of an adjacent segment. As further shown in FIGS. 3A and 3B, one end of the segment includes a set of tangs 130 and a set of notches 132 on the other end. The tangs 130 from one segment are received in the notches 132 of an adjacent segment to prevent the adjacent segments from axially rotating with respect to each other.

In the embodiment of the articulation joint body 100 shown in FIG. 3A, the outer wall 111A of the segment 110A at the proximal-most end of the articulation joint body 100 is adapted to receive the distal end of the shaft 21, and the outer wall 111B of segment 110B at the distal-most end of the articulation joint body 100 is adapted to receive the distal end 22 of the endoscope 20.

With reference now to FIG. 3B, also included adjacent to the first end 122 and second end 124 of the segments 110A, 110B are two or more slots 120 that each receive a cable guide element. In one embodiment the cable guide element is a seaming pin 150 that holds the adjacent segments together. As shown in FIG. 3C, the pin 150 has a head 152 sized to prevent the pin 150 from being pulled through the slot 120 and a tab 154 that fits into the slots 120 of the adjacent segments. The distal end of the tab 154 includes a hole 156 that forms a passage through which a control cable can be passed. In some embodiments, two slots 120 are spaced at a 180 degree interval around the circumference of each segment 110. In other embodiments, three slots 120 are spaced at 120 degree intervals around the circumference of each segment 110. In further embodiments, four slots 120 are spaced at 90 degree intervals around the circumference of each segment 110. In some embodiments, the outer extending portion of the slots 120 are a counter-bored detail for receiving the head 152 on the pin 150. In a preferred embodiment, the pins 150 are injection molded.

Figure 4:
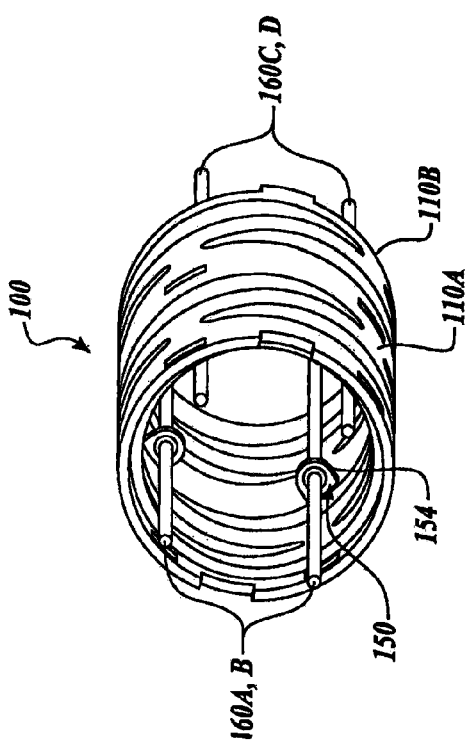
FIG. 4 is a partial perspective view of an articulation joint body comprising interconnected segments having four control cables threaded through four cable guide elements in accordance with an embodiment of the present invention.

FIG. 4 is a partial perspective view of two interconnected segments 110A, 110B, including pins 150 inserted into the slots with control cables 160A, 160B, 160C, 160D threaded through the holes 156 in the tabs 154 to couple the adjacent segments together. Variations in bending and torque fidelity along the length of the articulation joint can be achieved by varying the durometer rating of materials that are used to mold the different segments. Also, as mentioned above, the flexibility of the articulation joint may be varied by changing the distance between adjacent hinges in each segment and/or by varying the angles of the V-shaped slits that form the hinges.

Figure 5A:
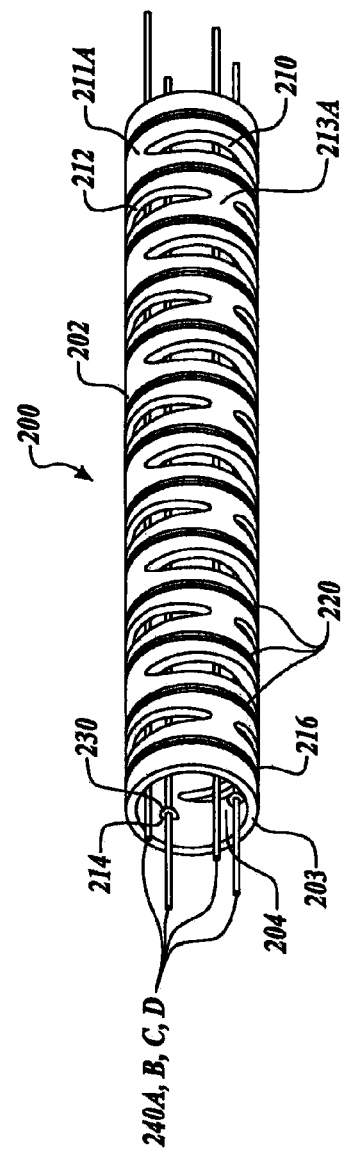
FIG. 5A is a perspective view of an embodiment of an articulation joint body comprising a unitary core having a plurality of annular rings fitted around the outer circumference of the unitary core at regular intervals, in accordance with an embodiment of the present invention.

FIG. 5A illustrates an articulation joint body 200 formed in accordance with another embodiment of the present invention. The articulation joint body 200 comprises an elongated unitary core 202 comprising a cylinder with an outer wall 203 and a central lumen 204. The outer wall 203 of the unitary core 202 comprises a series of hinges 210, 212 along its length that are oriented perpendicular to the longitudinal axis of the elongated unitary core 202. As shown in FIG. 5A, each hinge 210, 212 comprises a pair of opposing V-shaped slits in the outer wall 203 that are separated by a pair of opposing flex points 211A, 211B (hidden in FIG. 5A) and 213A, 213B (hidden in FIG. 5A) in the outer wall 203. In the embodiment of the articulation joint body 200 shown in FIG. 5A, the hinges 210 and 212 are arranged in an alternating 90 degree pattern, although other arrangements would also be known to one of skill in the art.

The outer wall 203 also includes a plurality of circumferential grooves 216 located on the outside of the outer wall 203 at intervals spaced along the length of the unitary core 202. Each circumferential groove 216 is sized to receive an annular ring 220, best shown in FIG. 5B. Each circumferential groove 216 further includes one or more slots 214, best shown in FIG. 5C. Each slot 214 is adapted to receive an inwardly extending cable guide loop 230 that fits through the slot 214 such that a control cable can fit in the space between the inner wall of the shaft and the enclosed portion of the loop 230. In one embodiment, one circumferential groove 216 is disposed between hinges 210 and 212 to form an alternating pattern, as shown in FIG. 5A.

The elongated unitary core 202 may be formed by injection molding using a suitable biocompatible polymeric material, such as polyurethane, polyethylene, polypropylene or other biocompatible polymers.

Figure 5C:
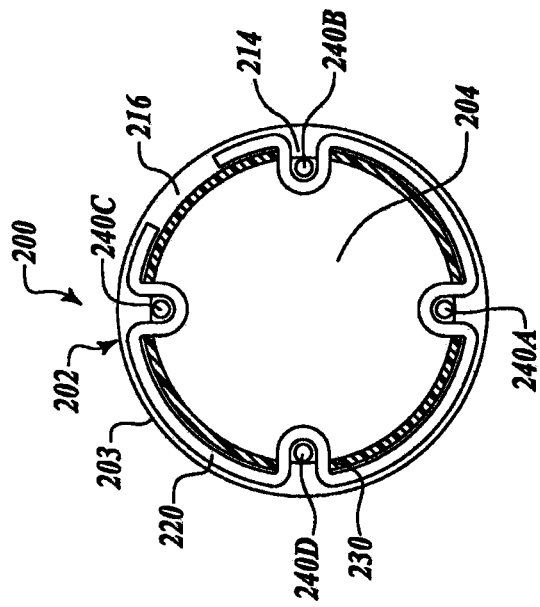
FIG. 5C is a cross-sectional view of the embodiment of the articulation joint body shown in FIG. 5A.
Figure 5B:
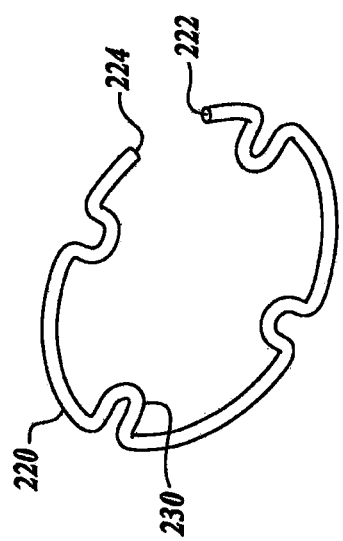
FIG. 5B is a detailed view of the embodiment of the annular ring shown in FIG. 5A.

FIG. 5B illustrates an embodiment of the annular ring 220 that comprises an outer circumference with a first end 222 and a second end 224 having a space therebetween that allows the annular ring 220 to be snap-fitted over the outer wall 203 of the unitary core 202. Positioned at equally spaced intervals around the outer circumference of the annular ring 220 are inwardly extending cable guide loops 230 that are adapted to be inserted into the corresponding slots 214 and are capable of receiving a control cable 240. One or more annular rings 220 may be disposed within the circumferential grooves 216 in the outer wall 203 of the unitary core 202, as shown in FIG. 5A.

In the embodiment shown in FIG. 5B, the annular ring 220 has four cable guide loops 230 inserted through the slots 214, through which four control cables 240A, 240B, 240C and 240D are threaded. However, a different number of cable guide loops and control cables may be provided, such as 2, 3, 4, or more than 4. The annular ring 220 may be made of a metal such as steel, brass, nitinol, etc., or molded from a biocompatible polymer.

FIG. 5C is a cross-sectional view of the articulation joint body 200 shown in FIG. 5A, showing the annular ring 220 fitted into the circumferential groove 216 formed in the outer wall 203 of the unitary core 202. In the embodiment shown, each circumferential groove 216 includes four slots 214. As shown, the four inwardly extending cable guide loops 230 protrude towards the central lumen 204 through the slots 214, to form guides through which control cables 240A, 240B, 240C and 240D are threaded.

Figure 6:
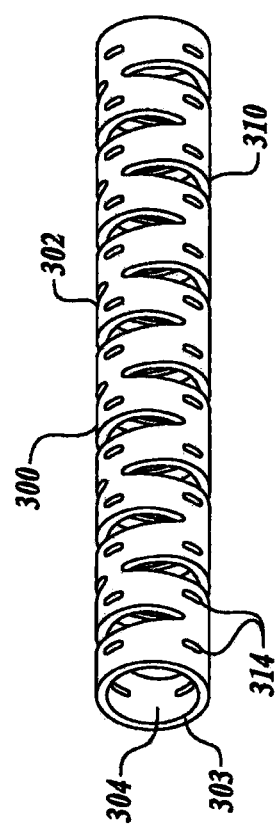
FIG. 6 is a perspective view of another embodiment of an articulation joint body comprising a unitary core having a plurality of slots, in accordance with an embodiment of the present invention.

FIG. 6 shows another embodiment of an articulation joint body 300 that has a unitary core 302 formed generally as a cylinder with an outer wall 303 and a central lumen 304. The articulation joint body 300 is substantially similar to the articulation joint body 200 described above, with the difference being that the plurality of circumferential grooves 216 are omitted in the joint body 300. A series of slots 314 are arranged around the outer circumference of the body 302 that are adapted to receive one or more cable guide loops 230 extending inward on the annular ring 220, as shown and described in reference to FIGS. 5A, 5B and 5C.

Figure 7:
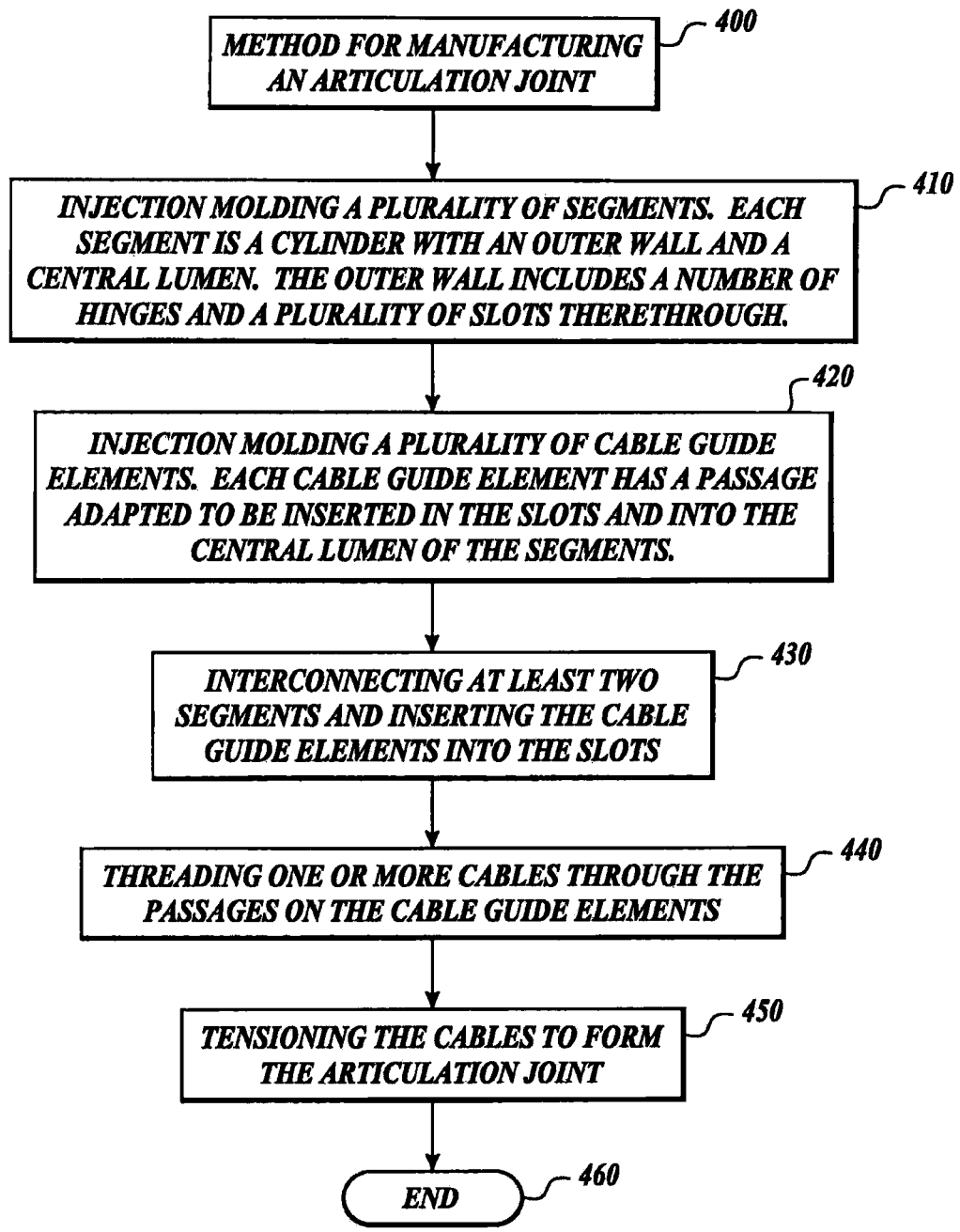
FIG. 7 is a flow diagram illustrating a method of manufacturing an articulation joint body having a plurality of interconnected segments in accordance with an embodiment of the present invention.

In another aspect, the present invention includes a method for manufacturing an articulation joint for use in a medical device, such as a low cost endoscope. FIG. 7 is a flow chart of a process for manufacturing a segmented articulation joint. The process begins at 400 and comprises injection molding a plurality of segments comprising corresponding interfacing tangs and notches at 410. The segments may be injection molded using a suitable biocompatible polymeric material, such as, for example, polyurethane, polyethylene, polypropylene or other biocompatible polymers. Each segment comprises a generally cylindrical body with an outer wall and a central lumen. The outer wall of each segment includes a number of hinge elements, such as V-shaped slits. The V-shaped slits may be molded into the segments or cut with a laser, waterjet or other material removal mechanism. In some embodiments, the outer walls of the segments further include a series of slots adapted to receive a cable guide element. The process further includes injection molding a plurality of cable guide elements at 420. In one embodiment, the cable guide elements include a retaining head connected to a passage sized to be received in the slots in the outer wall of the segments. The cable guide elements may be injection molded from a metal such as steel, brass, etc. or from a biocompatible polymer. At 430 a plurality of segments are interconnected by aligning the corresponding tangs and notches on each segment. Any number of segments may be connected together in order to provide various degrees of articulation. The passages of the plurality of guide elements are inserted into the slots on the interconnected segments. Once the cable guide elements are in place, cables are threaded through the corresponding cable passages at 440. The cables are then tensioned to form the articulation joint at 450. The cables are preferably made of a non-stretching material such as a stainless steel or a highly oriented polyethylene-terephthalate (PET) thread string. The method ends at 460.

Figure 8:
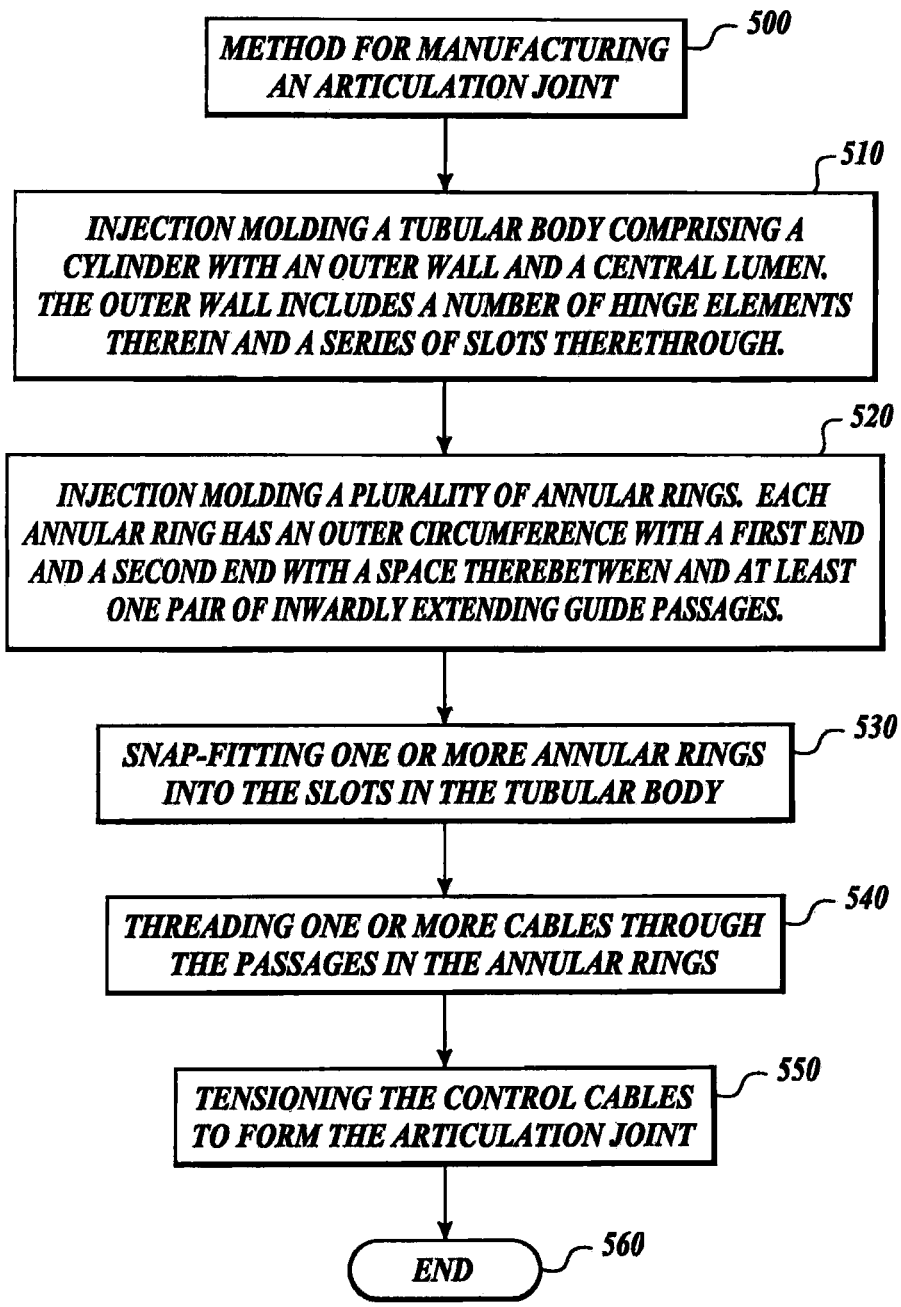
FIG. 8 is a flow diagram illustrating a method of manufacturing an articulation joint body having a unitary core in accordance with another embodiment of the present invention.

In another embodiment, the present invention provides a method for manufacturing an articulation joint comprising a unitary core as shown in FIG. 8. The process starts at 500 and comprises injection molding a tubular body comprising a cylinder with an outer wall and a central lumen. The outer wall comprises a plurality of hinge elements such as V-shaped slits. In one embodiment, the outer wall includes a series of slots arranged around the circumference of the outer wall that are each adapted to receive a guide passage on an annular ring. In another embodiment, the outer wall further includes a series of circumferential grooves that are disposed over the slots. At 520 the process further includes injection molding, stamping, or otherwise forming a plurality of annular rings that each comprise an outer circumference with a first end and a second end having a space therebetween that allows the ring to be snap-fitted over the outer wall and received in one of the circumferential grooves. Each annular ring also includes two or more oppositely formed, inwardly extending guide passages that are adapted to be received in the slots in the outer wall. The annular rings may be formed from a metal such as steel, brass, etc. or from a biocompatible polymer. At 530 the plurality of annular rings are snap-fitted over the tubular body such that the guide passages extend through the slots towards the central lumen. Once the annular rings are in place, one or more cables are threaded through the guide passages at 540. The threaded cables are then tensioned at 550 to form an articulation joint. The process ends at 560.

While the preferred embodiment of the invention has been illustrated and described, it will be appreciated that various changes can be made therein without departing from the scope of the invention. It is therefore intended that the scope of the invention be determined from the following claims and equivalents thereof.

The embodiments of the invention in which an exclusive property or privilege is claimed are defined as follows:

1. An articulation joint comprising:
   a tubular body comprising a cylinder with an outer wall and a central lumen, wherein the outer wall includes a plurality of hinge elements therein and a series of slots therethrough, the plurality of hinge elements comprising a series of opposing pairs of V-shaped slits oriented transverse to a longitudinal axis of the tubular body;

a plurality of annular rings around a circumference of the outer wall of the tubular body at spaced intervals, each annular ring comprising at least one pair of inwardly extending guide passages inserted into the slots in the tubular body; and at least two control members, wherein each control member is threaded through one guide passage of the pair of guide passages of each annular ring.

2. The articulation joint of claim 1, wherein each annular ring comprises an outer circumference with a first end and a second end having a space therebetween sized to allow the annular ring to be snap-fitted over the tubular body.

3. The articulation joint of claim 2, wherein the tubular body further comprises a series of circumferential grooves formed in the outer wall, wherein the circumferential grooves are adapted to receive the annular rings.

4. The articulation joint of claim 3, wherein each circumferential groove includes one or more slots of the series of slots.

5. The articulation joint of claim 3, wherein at least one groove of the series of circumferential grooves is disposed between two hinge elements of the plurality of hinge elements to form an alternating pattern.

6. The articulation joint of claim 1, wherein each annular ring includes two pairs of guide passages.

7. The articulation joint of claim 1, wherein the series of opposing pairs of V-shaped slits are oriented to provide flexibility along a first axis, and wherein the tubular body further includes at least one opposing pair of V-shaped slits oriented to provide flexibility along a second axis orthogonal to the first axis.

8. The articulation joint of claim 7, wherein a number of the slots in the outer wall of the tubular body are circumferentially disposed between one opposing pair of V-shaped slits oriented to provide flexibility along the first axis and one opposing pair of V-shaped slits oriented to provide flexibility along the second axis.

9. The articulation joint of claim 1, wherein the tubular body is molded.

10. The articulation joint of claim 9, wherein the tubular body is molded from a biocompatible polymeric material.

11. The articulation joint of claim 1, wherein the plurality of annular rings are metal.

12. The articulation joint of claim 1, wherein the articulation joint comprises at least two segments molded from polymeric materials having durometer values that differ from one another.

13. An articulation joint comprising:

a tubular body comprising a cylinder with an outer wall and a central lumen, wherein the outer wall includes a plurality of hinge elements and a plurality of slots, wherein each hinge element is integral with an adjacent hinge element;

a plurality of annular rings coupled to the tubular body around a circumference of and radially outside the outer wall at spaced intervals along a longitudinal axis of the tubular body, each annular ring comprising at least two inwardly extending guide passages, each guide passage being inserted into one of the slots of the plurality of slots; and at least two control members, each control member extending through one of the guide passages of each annular ring.

14. The articulation joint of claim 13, wherein each slot of the plurality of slots is disposed between two of the hinge elements along the longitudinal axis of the tubular body.

15. The articulation joint of claim 13, wherein the tubular body includes a series of two slits spaced 180 degrees apart about the circumference of the outer wall.

16. The articulation joint of claim 15, wherein each slit is V-shaped.

17. The articulation joint of claim 13, wherein the outer wall of the tubular body includes a plurality of slits, the tubular body further including a series of three slots spaced 120 degrees apart about the circumference of the outer wall.

18. The articulation joint of claim 13, wherein the tubular body comprises a plurality of segments each extending from a first end to a second end, each segment including at least two hinge elements between the first end and the second end, and at least one slot between the at least two hinge elements and the first end.

19. An articulation joint comprising:

a tubular body comprising a cylinder with an outer wall and a central lumen, wherein the outer wall includes a plurality of hinge elements therein and a series of slots therethrough;

a plurality of annular rings around a circumference of the outer wall of the tubular body at spaced intervals, each annular ring comprising at least one pair of inwardly extending guide passages; and at least two control members, wherein each control member extends through one guide passage of the pair of guide passages of each annular ring;

wherein an outermost surface of outer wall defines a plurality of circumferential grooves, each groove includes at least two slots of the plurality of slots, and each annular ring is disposed in one of the grooves such that the pair of guide passages are inserted into the slots in the tubular body.

20. The articulation joint of claim 19, wherein each annular ring extends circumferentially from a first end to a second end having a space therebetween to allow the annular ring to be snap-fitted over the tubular body.

* * * * *